(12) United States Patent
Van Dyke

(10) Patent No.: US 6,528,519 B1
(45) Date of Patent: Mar. 4, 2003

(54) USE OF TETRANDRINE AND ITS DERIVATIVES TO TREAT MALARIA

(76) Inventor: Knox Van Dyke, 106 Morgan Dr., Morgantown, WV (US) 26505

( * ) Notice: Subject to any disclaimer, the term of this patent is extended or adjusted under 35 U.S.C. 154(b) by 0 days.

(21) Appl. No.: 07/660,807

(22) Filed: Feb. 28, 1991

Related U.S. Application Data

(62) Division of application No. 07/413,711, filed on Sep. 28, 1989, now Pat. No. 5,025,020.

(51) Int. Cl.$^7$ ................................................ A61K 31/44
(52) U.S. Cl. ........................ 514/280; 514/280; 514/281; 514/895
(58) Field of Search ................................ 514/895, 280, 514/281

(56) References Cited

PUBLICATIONS

Fournet Et Al, 1988, Antiparisitic Activity of Bisbenzyliso-quine Alkaloids I., Journal of Ethnopharmacology, vol. 24, pp. 327–335 (English Translation).*
Fournet Et Al, 1988, Antiparisitic Activity of Bisbenzyliso-quinoe Alkaloids II Journal of Ethnopharmacology, vol. 24, pp. 337–343 (English Translation).*
Riou Et Al, 1986, Purification and Characterization of *Plasmodium berghei* DNA Topoisomerases I and II: Biochemistry, vol. 25, No. 7, pp. 1471–1479.*
Fournet Et Al 110 CA: 132057y 1980.*
Fournet Et Al 110 CA: 1322058z 1988.*
Neal Et Al, Transactions of Royal Society of Tropical Medicine & Hygiene (1989) vol. 83 pp. 197–198.*
*The Merck Index*, Eleventh Edition, notes 1168–1169.
*Bacteriology Principles And Practice*, Barnes & Noble, pp. 318–319.
*Biochemical And Biophysical Research Communications*, vol. 155, No. 1, 1988, pp. 476–481.
"A New Calcium Antagonist of Chinese Medicinal Origin: Tetrandrine," Fang et al.
"Chemical Studies On Qinghaosu (Artemisinine)," *Journal of Traditional Chinese Medicine*, 2(1):3–8, 1982.
"The Chemistry And Synthesis Of Quinghaosu Derivatives," *Journal of Traditional Chinese Medicine*, 2(1):9–16, 1982.
"Qinghaosu (Artemisinin): An Antimalarial Drug from China," *Science*, vol. 228, pp. 1049–1055.
"Antimalarial Efficacy And Mode Of Action Of Qinghaosu And Its Derivatives In Experimental Models," *Journal of Traditional Chinese Medicine*, 2(1):17–24, 1982.
"Clinical Studies On The Treatment Of Malaria With Qinghaosu And Its Derivatives," *Journal of Traditional Chinese Medicine*, 2(1):45–50, 1982.
The *Mayo Clinic Family Healthbook*, pp. 868–869, ©1990.
*Modern Pharmacology*, Third Edition, ©1990, Chapter 56.

* cited by examiner

*Primary Examiner*—Russell Travers
(74) *Attorney, Agent, or Firm*—Price, Heneveld, Cooper, DeWitt & Litton

(57) ABSTRACT

The specification discloses the treatment of malaria through the use of tetrandrine and its derivatives.

24 Claims, 1 Drawing Sheet

USE OF TETRANDRINE AND ITS DERIVATIVES TO TREAT MALARIA

CROSS REFERENCE TO RELATED APPLICATION

This is a division of application Ser. No. 07/413,711, filed Sep. 28, 1989, now U.S. Pat. No. 5,025,020.

This application is based on the inhibitory activity of tetrandrine and all of its derivatives, specifically against malaria, as well as the ability of such derivatives, some in particular, to potentiate the effectiveness of antimalarial drugs against multidrug resistant malarial cells in particular. A related application filed concurrently herewith discloses and claims the generic ability of methoxadiantifoline, tetrandrine and certain of its derivatives to potentiate the inhibitory action of primary drugs against multidrug resistant cells generically, and to apparently reverse the normal pump out action of P-glycoprotein in such cells.

BACKGROUND OF THE INVENTION

A number of diverse drugs have been found effective against malaria. However in many cases, the initial success of physicians in treating this disease is followed by total failure. Drugs which worked initially become totally ineffective after a period of time. An initial period of remission is often followed by a period of frustration during which nothing seems to be effective against the disease. Death becomes inevitable.

Such a phenomenon is often referred to as multidrug resistance. A malarial cell which initially responds to treatment by one or more drugs becomes resistant to treatment by not only the drugs previously used, but but any malarial treatment drug. Martin, Odula and Milhous disclosed the treatment of such multidrug resistance in malaria by using verapamil. "Reversal of Chloroquine Resistance in *Plasmodium falciparaum* by Verapamil," Martin et al, Science, Feb. 28, 1987. Martin et al, reports that Verapamil did reverse chloroquine resistance in malaria cells, but that the verapamil alone had no effect on the malaria. The structural formula of verepamil is shown below:

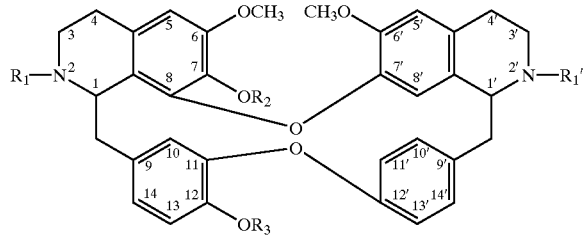

The problem with this approach is that verapamil is a calcium channel blocker. While calcium channel blockers are therapeutic in the treatment of hypertension at moderate levels, they are toxic at levels high enough to effect MDR reversal.

Consequently, researchers throughout the world continue to press for techniques for reversing multidrug resistance. A successful clinical technique for reversing multidrug resistance in malaria will be one of the most important breakthroughs in the fight against malaria.

SUMMARY OF THE INVENTION

In the present invention, it has been surprisingly found that tetrandrine and its derivatives act to reverse multidrug resistance in malaria and do not show an affinity for calcium channel blocking. Thus the toxicity problems associated with verapamil and its derivatives are avoided.

Perhaps even more surprisingly, it has been found that tetrandrine and its derivatives are also specifically effective against malaria, including multidrug resistant strains, even in the absence of primary treatment drugs. Indeed, the most surprising of all is that the most preferred tetrandrine type structure is actually more effective against multidrug resistant malarial strains than it is against drug sensitive strains.

These surprising and unexpected results, as well as other objects, advantages and features of the present invention will be more fully understood and appreciated by reference to the Description of the Preferred Embodiment and appended drawings.

BRIEF DESCRIPTION OF THE DRAWINGS

FIG. 1 is an isobologram showing the effectiveness of tetrandrine and chloroquine at 50% inhibition concentrations against sensitive and resistant malarial strains;

FIG. 2 is an isobologram showing the effectiveness of tetrandrine and qinghaosu at 50% inhibition concentrations against sensitive and resistant malarial strain.

DESCRIPTION OF THE PREFERRED EMBODIMENT

In the preferred embodiment, the compounds of the present invention have the following structural formula:

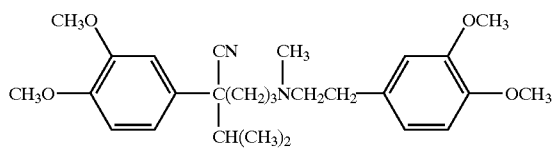

where $R_1$ and $R_1'$ are the same or different shortchained carbon based ligand including, without limitation, $CH_3$, $CO_2CH_3$, or H; and $R_2$ and $R_3$ are the same or different CH3 or Hydrogen.

This family of compounds includes tetrandrine, isotetrandrine, hernandezine, berbamine, pycnamine, phaeanthine, obamegine, and fangchinoline, which list is not intended to be exhaustive. In all of the these examples, $R_1$ and $R_1'$ constitute the methyl group.

Variation within the group occurs in that $R_2$ and $R_3$ may constitute either a methyl group or hydrogen and the isomeric configuration of the compounds at the C-1 and C-1' chiral carbon positions is either R (rectus) or S (sinister). The rules for R and S configuration can be found in Morrison and Boyd, "Organic Chemistry," 4th Edition, Copyright 1983 by Allyn and Bacon, at pages 138–141. In addition, hernandezine includes a methoxy group at the C-5 position, a substitution which does not appear to be significant In the operability of the compound in the present invention. The specific manner in which these exemplary family members very is set forth in Table V below, wherein these family members are compared to two non-family members for activity against drug sensitive and drug resistant strains of P. falciparum malaria.

A specific in vivo dosage for each of the various members of the tetrandrine family for reversing malarial multidrug resistance and/or for specifically treating malaria has not been established. However, such dosage can be established through routine clinical experimentation by referencing the concentrations at which the various compounds have exhibited 50% inhibition as set forth Tables I through V herein. These concentrations hove been from about 0.1 to about 3 micro molar. Such concentrations can be achieved in vivo by administering dosages of from about 100 to about 300 mg/deg. It Is known that at these concentrations, tetrandrine is substantially non-toxic. The preferred method for administering the drug is orally, though other methods such as injection may be used.

Prior studies of tetrandrine for various other uses have indicated a minimal toxicity at doses of from 100 to 300 mg/day. Tetrandrine and several tetrandrine derivatives were screened for calcium channel blocker activity, and such was found to be minimal. Thus, the toxicity problems associated with higher doses of calcium channel blockers such as verapamil ore not observed in members of the tetrandrine family.

The effectiveness of tetrandrine in reversing malarial multidrug resistance was determined by comparing the antimalarial action of tetrandrine and chloroquine alone and in combination against a *P. falciparum* malarial strain which is sensitive to Chloroquine and another which is resistant to chloroquine. A similar study was conducted using tetrandrine and qinghaosu. Chloroquine and Qinghaosu are commonly used antimalaria drugs.

unincorporated material is washed away. In the absence of drug there is 100% incorporation of the labeled material. When drugs interfere (directly or indirectly), an inhibitory dose of 50% ($IC_{50}$) can be calculated. The experiments were repeated three times except where noted. Statistical analysis was done using Student's t test for significance. Van Dyke et ea., "Exp. Parasitol.," Vol 64, 418–423 (1987).

Figures 1, 2:
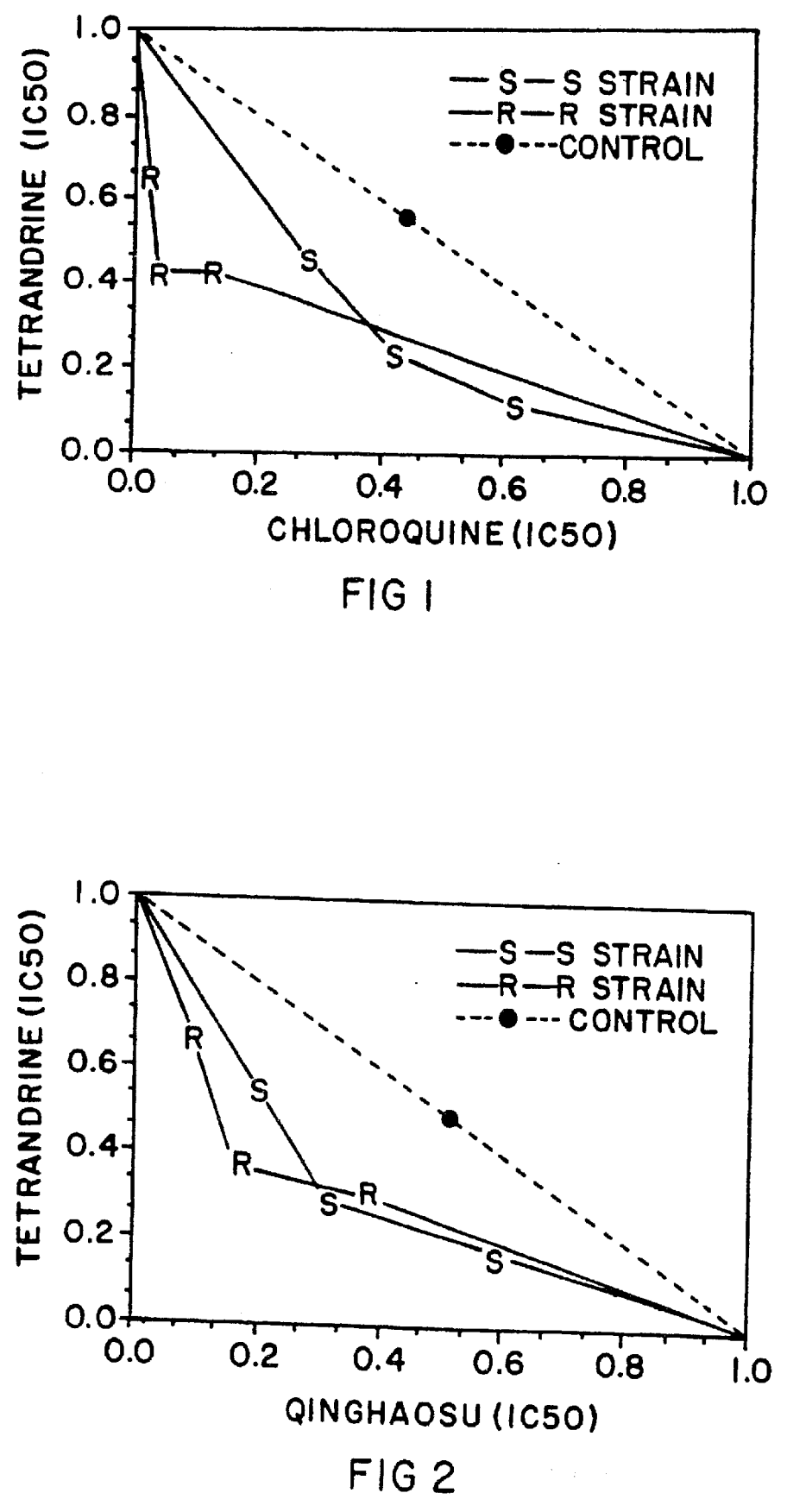

Tetrandrine completely reversed resistance to chloroquine in chloroquine-resistant malaria. When tetrandrine Is added to Chloroquine, it supplements and potentiates the antimalarial activity. When tetrandrine is added to Qinghaosu, it provides long-acting and synergistic activity to Qinghaosu. This can be seen In Tables I, II, III, and IV while isobolograms (FIGS. 1 and 2) of Tetrandrine and Chloroquine as well as Tetrandrine and Qinghaosu reveal the synergistic and potentiating activity of Tetrandrine when added to Chloroquine or Qinghaosu. Remarkably, when $3.0\mu$ Molar Tetrandrine is added to $0.1\mu$ Molar Chloroquine, the $IC_{50}$ of Chloroquine con be lowered 43-Fold.

TABLE 1.

$IC_{50}$ (nM) OF TT AND CQ FOR EACH DRUG ALONE AND IN COMBINATION*

| | SINGLE DRUG | | DRUG COMBINATION** | | |
|---|---|---|---|---|---|
| | | | TT (1.0 uM) | TT (2.0 uM) | TT (3.0 uM) |
| MALARIA*** | TT | CQ | CQ (0.3 uM) | CQ (0.2 uM) | CQ (0.1 uM) |
| S STRAIN | 498.1 ± 93.7 | 26.7 ± 3.8 | 54.9 ± 7.1 (TT) 16.5 ± 2.1 (CQ) | 114.1 ± 23.0 (TT) 11.4 ± 2.3 (CQ) | 223.3 ± 38.6 (TT) 7.4 ± 1.3 (CQ) |
| R STRAIN | 197.5 ± 24.7 | 185.8 ± 4.9 | 79.5 ± 13.7 (TT) 23.8 ± 4.1 (CQ) | 79.5 ± 16.1 (TT) 8.0 ± 1.6 (CQ) | 124.6 ± 9.6 (TT) 4.2 ± 0.3 (CQ) |

*The data in the table above are the mean values ± S.D. (nM) from three experiments except where noted.
**Ratios of TT/CQ in the drug combinations are 10:3, 10:1 and 30:1 respectively.
***S and R strains represent CQ-sensitive (FCMSU1/Suden) and resistent (w2) strain of *P. falciparum* respectively.

The dose ($IC_{50}$) of each drug or each drug combination required to effect a 50% inhibition in the malarial activity of each strain was determined by establishing a dose response curve for each.

FCMSUI/Sudan strain and cloned Inochina (W-2) strain of *P. falciparum* were used. The former is sensitive to chloroquine and the latter is resistant to chlororquine. The two strains of the parasite were cultured according to the candle jar method of Trager and Jensen, Science 193, 673–675, 1976. In a given experiment, 4-day-old Petri dish cultures (approx. 10% parasitemia) were diluted with medium containing an amount of noninfected type A human erythrocytes to obtain a culture with a final hematocrit of 1.5% and parasitemia of 0.5–10%. The resulting culture was ready for addition to microtitration plates with 96 flat-bottom wells.

The testing procedure used was similar to that described by Desjardins et al., in Antimicrobial Agents and Chemotherapy, 16, 710–718 (1979). Briefly, the final volume added to each of the 96-well micrtitration plates was 250 µl and consisted of 25 µl of complete medium with or without the primary drug (chloroquine or qinghaosu), 175 µl of either the parasitized culture or a nonparasitized human erythrocyte control, and 25 µl of complete medium with or without tetrandrine. 25 µl radioactive (0.5 µCl) [2,8-³H] adenosine. The microtitration plates were incubated in a candle jar for an additional 18 hr, at 37° C.

As the malaria parasite grows ³H-adenosine is metabolized and incorporates into polymeric RNA and DNA. The labeled polymers are trapped on glass fiber filters and When the inhibiting activity of two drugs eg A and B are compared, the middle point of the dose response curve is usually chosen as the basis for comparison. This point is known as the inhibitory dose that occurs at the point of 50% inhibition of the response to be measured (inhibitory concentration at 50% Inhibitory response=$IC_{50}$) An isobologrom is developed by comparing the $IC_{50}$ of one drug against the other ie drug A against Drug B. We start by putting the $IC_{50}$ of Drug B at the top of the y axis marked I.O. The $IC_{50}$ of Drug A Is placed at the position 1.0 on the x axis. The combinations of Drug A and Drug B are mixed and tested that are below $IC_{50}$ of either drug and the points are located on the graph. If the two. drugs are additive there is a straight line between the $Y_1X_0$ (Drug B) and $Y_0X_1$ (Drug A). It the line or curve bends below the straight line the drugs are synergistic or potentiating. If the line bends above the straight line the two drugs are antagonistic.

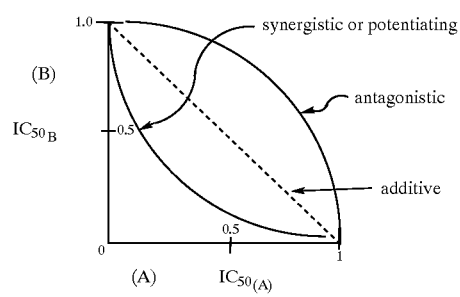

TABLE 2.

IC$_{50}$ (nM) OF TT AND QHS FOR EACH DRUG ALONE AND IN COMBINATION*

| | SINGLE DRUG | | DRUG COMBINATION** | | |
|---|---|---|---|---|---|
| | | | TT (1.0 uM) | TT (2.0 uM) | TT (3.0 uM) |
| MALARIA*** | TT | QHS | QHS (0.3 uM) | QHS (0.2 uM) | QHS (0.1 uM) |
| S STRAIN | 410.2 ± 69.0 | 36.7 ± 4.7 | 71.9 ± 8.9 (TT) | 113.5 ± 6.3 (TT) | 219.5 ± 35.5 (TT) |
| | | | 21.6 ± 2.7 (QHS) | 11.4 ± 0.6 (QHS) | 7.3 ± 1.2 (QHS) |
| R STRAIN | 205.6 ± 49.8 | 47.8 ± 14.5 | 59.6 ± 13.7 (TT) | 71.8 ± 13.8 (TT) | 136.9 ± 41.6 (TT) |
| | | | 17.9 ± 4.1 (QHS) | 7.2 ± 1.4 (QHS) | 4.6 ± 1.4 (QHS) |

*The data in the table above are the mean values ± S.D. (nM) from three experiments except where noted.
**Ratios of TT/QHS in the drug combinations are 10:3, 10:1 and 30:1 respectively.
***S and R strains represent CQ-sensitive (FCMSU1/Suden) and resistant (W2) strain of *P. falciparum* respectively.

TABLE 3.

EFFECT OF COMBINATION OF TETRANDRINE AND CHLORQUINE ON *P. FALCIPARUM*

| | | SFIC* | | |
|---|---|---|---|---|
| | | 1.0 uM TT | 2.0 uM TT | 3.0 uM TT |
| MALARIA** | TRIAL | 0.3 uM CQ | 0.2 uM CQ | 0.1 uM CQ |
| S STRAIN | 1 | 0.77 | 0.66 | 0.73 |
| | 2 | 0.64 | 0.77 | 0.70 |
| | 3 | 0.78 | 0.55 | 0.75 |
| | MEAN ± S.D. | 0.73 ± 0.06 | 0.66 ± 0.09 | 0.73 ± 0.02 |
| R STRAIN | 1 | 0.60 | 0.45 | 0.74 |
| | 2 | 0.68 | 0.63 | 0.76 |
| | 3 | 0.36 | 0.30 | 0.50 |
| | MEAN ± S.D. | 0.55 ± 0.14 | 0.46 ± 0.14 | 0.67 ± 0.12 |

*SFIC represents sum of fractional inhibitory concentration as described by Berenbaum (11), SFIC is equal to one in cases of additive effects of the drugs, higher than one in cases of antagonism and lower than one in synergistic action.
**S and R strain: chloroquine sensitive (FCMSU1/Suden) and resistant (W2) strain of *P. falciparum*.

TABLE 4.

EFFECT OF COMBINATION OF TETRANDRINE AND QINGHAOSU ON *P. FALCIPARUM*

| | | SFIC* | | |
|---|---|---|---|---|
| | | 1.0 uM TT | 2.0 uM TT | 3.0 uM TT |
| MALARIA** | TRIAL | 0.3 uM QHS | 0.2 uH QHS | 0.1 uM QHS |
| S STRAIN | 1 | 0.77 | 0.68 | 0.71 |
| | 2 | 0.74 | 0.49 | 0.72 |
| | 3 | 0.79 | 0.62 | 0.77 |
| | MEAN ± S.D. | 0.77 ± 0.02 | 0.60 ± 0.08 | 0.73 ± 0.03 |
| R STRAIN | 1 | 0.63 | 0.46 | 0.71 |
| | 2 | 0.77 | 0.72 | 0.74 |
| | 3 | 0.64 | 0.40 | 0.81 |
| | MEAN ± S.D. | 0.68 ± 0.06 | 0.52 ± 0.14 | 0.75 ± 0.04 |

*SFIC represents sum of fractional inhibitory concentration as described by Berenbaum (11), SFIC is equal to one in cases of additive effects of the drugs, higher than one in cases of antagonism and lower than one in synergistic action.
**S and R strain: chloroquine sensitive (FCMSU1/Suden) and resistant (w2) strain of *P. falciparum*.

Tetrandrine and various of its derivatives were also compared to non-tetrandrine derivatives for their effectiveness against a chloroquine sensitive and a chloroquine resistant strain of *P. falciparum* malaria. The test procedure was basically the same as outlined above. The non family members were cycleanine and cepharanthine, whose structural formulas are illustrated below:

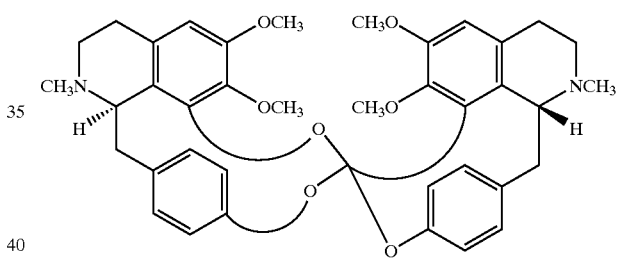

Structure of cycleanine

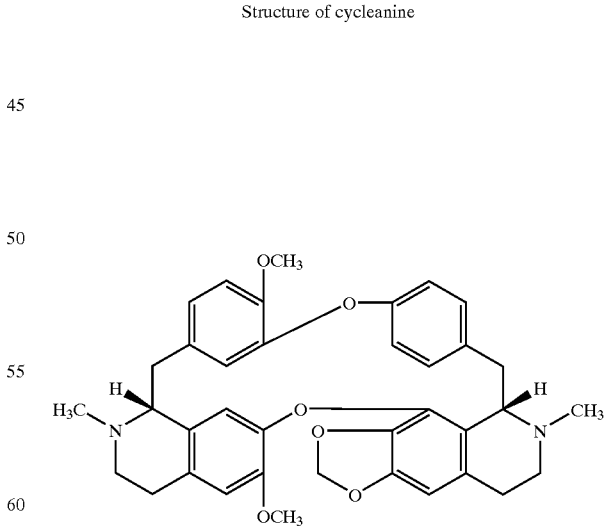

Structure of cepharanthine

These comparative activities are set forth in Table V below.

TABLE V

CHEMICAL STRUCTURE-ANTIMALARIAL ACTIVITY OF BISBENZYLISOQUINOLINE ALKALOIDS AGAINST PLASMODIUM FALCIPARUM IN VITRO

| Drug | Configuration | | | Substituents | | | Oxygen | $IC_{50}$ $(10^{-7}M)$ | | Ratio |
|------|------|------|------|------|------|------|------|------|------|------|
| (a) | C-1 | C-1* | C-5 | C-7 | C-12 | C-5* | Bridge | S** | R** | (S/R)* |
| TT | S | S | H | OCH3 | OCH3 | | C8-C7* C11-C12* | 2.9 | 1.2 | 2.6 |
| IT | R | S | H | OCH3 | OCH3 | | C8-7* C11-C12* | 4.8 | 1.4 | 3.5 |
| HE | S | S | OCH3 | OCH3 | OCH3 | | C8-C7* C11-C12* | 3.7 | 1.3 | 2.8 |
| BB | R | S | H | OCH3 | OH | | C8-C7* C11-C12* | 4.6 | 1.9 | 2.7 |
| PY | R | R | H | OCH3 | OH | | C8-C7* C11-C12 | 3.8 | 4.2 | 0.9 |
| PH | R | R | H | OCH3 | OCH3 | | C8-C7* C11-C12 | 6.0 | 5.0 | 1.2 |
| OB | R | S | H | OH | OH | | C8-C7* C11-C12* | 6.6 | 4.8 | 1.5 |
| FA | S | S | H | OH | OCH3 | | C8-C7* C11-C12* | 2.6 | 2.2 | 1.2 |
| CY | R | R | H | OCH3 | | | C8-C12* C12-C8* | 32 | 42 | 0.8 |
| CE | S | R | H | OCH2 | | | C8-C7* C12-C11* | 10 | 9.4 | 1.1 |

(a) TT-tetrandrine; IT-iSotetrandrine; HE-hernandezine; BB-berbamine; PY-pycnamine; PH-phaeanthine; OB-obamegine; FA-fangchinoline; CY-cycleanine; CE-cepharanthine.
*$IC_{50}$ of a drug against sensitive strain of *P. falciparum* is divided by $IC_{50}$ for resistant strain.
**S and R represent chloroquine-sensitive and resistant strain of *P. falciparum*.

The results of Table V show that tetrandrine and its derivatives are for more effective against either the chloroquine sensitive malarial strain or the chloroquine resistant strain then are either cycleanine or cepharanthine. Cepharanthine was the better of the non family compounds, and $9.4 \times 10^{-7}$ moles were required to effect a 50% inhibition in activity in the resistant strain, as compared to $5 \times 10^{-7}$ moles of phaeanthine, the least effective member of the tetrandrine family. The performance of cycleanine was much worse, requiring 3 to 4 times the quantity of cepharanthine to effect 50% inhibition.

The results of Table V also illustrate that those members of the tetrandrine family having the "S" isomeric configuration at the C-1 chiral carbon and having at least one of the $R_2$ and $R_3$ substituents comprising $CH_3$ are the most effective members of the family against the chloroquine resistant malarial strains. Further where $R_2$ specifically constitutes a $CH_3$ substituant, the tetrandrine family member is actually substantially more effective ogolnst the chloroquine resistant malarial strain than it is against the chloroquine sensitive malarial strain. This extremely surprising result suggests that these family members would also be the most effective members of the family in effecting multidrug resistance reversal. Thus, the preferred tetrandrine family members have the "S" configuration at the C-1' carbon location and have at least one of $R_2$ and $R_3$ comprising $CH_3$, and most preferably with at least $R_2$ comprising $CH_3$.

Of course it is understood that the above is merely a preferred embodiment of the invention and that various changes and alterations can be mode without departing from the spirit and the broader aspects thereof.

I claim:

1. A method for reversing cell multidrug resistance in malaria comprising: exposing multidrug resistant cells to effective concentrations of a compound having the following formula:

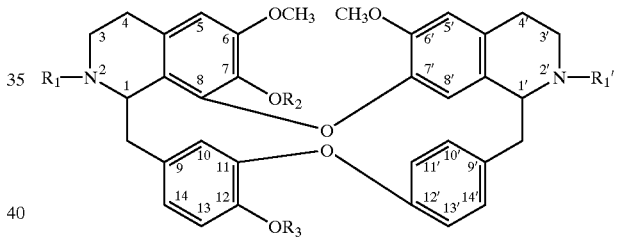

where $R_1$ end $R_1'$ are the same or different shortchained carbon based ligand; and $R_2$ and R3 are the same or different $CH_3$ or Hydrogen.

2. The Method of claim 1 where: the isomeric configuration at the C-1 chiral carbon location is "S" and at least one of $R_2$ and $R_3$ comprises $CH_3$.

3. The Method of claim 2 where: $R_2$ comprises $CH_3$.

4. The Method of claim 3 in which sold compound comprises tetrandrine.

5. The Method of claim 4 in which sold compound is administered at a dosage level of from about 100 to about 300 mg per day.

6. The Method of claim 4 wherein the use of said compound is combined with the use of at least one principal drug known to be effective for treating malaria.

7. The Method of claim 3 in which sold compound Is administered at a dosage level of from about 100 to about 300 mg per day.

8. The Method of claim 3 wherein the use of said compound is combined with the use of at least one principal drug known to be effective for treating malaria.

9. The Method of claim 2 in which sold compound is administered at a dosage level of from about 100 to about 300 mg per day.

10. The Method of claim 2 wherein the use of said compound is combined with the use of at least one principal drug known to be effective for treating malaria.

11. The Method of claim 1 in which said compound is administered at a dosage level of from about 100 to about 300 mg per day.

12. The Method of claim 1 wherein the use of said compound is combined with the use of at least one principal drug known to be effective for treating malaria.

13. A method for treating malaria comprising: exposing malaria cells to effective concentrations of a compound having the following formula:

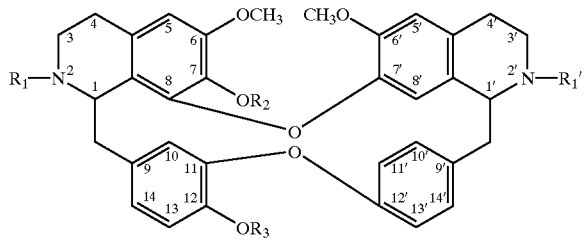

where $R_1$ and $R_1$, are the same or different shortchained carbon based ligand; and $R_2$ and $R_3$ are the same or different $CH_3$ or Hydrogen; wherein the use of said compound is combined with the use of at least one additional principal drug known to be effective for treating malaria.

14. The Method of claim 13 wherein said principal drug is selected from the group consisting of chloroquine, ginghoasu and mixtures thereof.

15. The Method of claim 19 in which said compound is used at dosage level of from about 100 to about 300 mg per day.

16. The Method of claim 13 in which said compound is used at dosage level of from about 100 to about 300 mg per day.

17. The Method of claim 13 where: the isomeric configuration of the C-1' chiral carbon location is "S" and at least one of $R_2$ and $R_3$ comprises $CH_3$.

18. The Method of claim 17 where: $R_2$ comprises $CH_3$.

19. The Method of claim 18 in which said compound comprises tetrandrine.

20. The Method of claim 19 in which said compound is used at dosage level of from about 100 to about 300 mg per day.

21. The Method of claim 20 wherein said principal drug is selected from the group consisting of chloroquine, ginghoasu and mixtures thereof.

22. The Method of claim 19 wherein said principal drug is selected from the group consisting of chloroquine, ginghoasu and mixtures thereof.

23. The Method of claim 18 wherein said principal drug is selected from the group consisting of chloroquine, ginghoasu and mixtures thereof.

24. The Method of claim 17 wherein said principal drug is selected from the group consisting of chloroquine, ginghoasu and mixtures thereof.

* * * * *

UNITED STATES PATENT AND TRADEMARK OFFICE
CERTIFICATE OF CORRECTION

PATENT NO. : 6,528,519 B1
DATED : March 4, 2003
INVENTOR(S) : Knox Van Dyke

It is certified that error appears in the above-identified patent and that said Letters Patent is hereby corrected as shown below:

Column 2,
Line 64, "hove" should be -- have --.

Column 3,
Line 10, "ore" should be -- are --.
Line 42, "FCMSUI/Sudan" should be -- FCMSU1/Sudan --.
Line 51, "0.5-10%" should be -- 0.5-1.0% --.

Column 4,
Lines 6-7, "et ae.," should be -- et al., --.
Line 20, "con" should be -- can --.
Line 36, "Suden" should be -- Sudan --.
Lines 43-44, "isobologrom" should be -- isobologram --.
Line 50, after "two" delete ".".
Line 52, "It" should be -- If --.

Column 5,
Lines 16, 43 and 65, "Suden" should be -- Sudan --.
Line 52, "0.2 uH QHS" should be -- 0.2 uM QHS --.

Column 7,
Line 23, Table V, "OCH2" should be -- OCH2-(ring) --.
Line 33, "for" should be -- far --.
Line 45, "C-1" should be -- C-1' --.
Line 50, "ogolnst" should be -- against --.
Line 61, "mode" should be -- made --.

Column 8,
Line 43, "end" should be -- and --.
Lines 49, 51, 57 and 63, "sold" should be -- said --.

UNITED STATES PATENT AND TRADEMARK OFFICE
CERTIFICATE OF CORRECTION

PATENT NO.  : 6,528,519 B1
DATED       : March 4, 2003
INVENTOR(S) : Knox Van Dyke It is certified that error appears in the above-identified patent and that said Letters Patent is hereby corrected as shown below:

Column 9,
Line 22, "$R_1$ and $R_1$" should be -- $R_1$ and $R_{1'}$ --.
Lines 28-29, "ginghoasu" should be -- qinghoasu --.

Column 10,
Line 1, "19" should be -- 14 --.
Lines 17-18, 20-21 and 26-27, "ginghoasu" should be -- qinghoasu --.
Lines 23-24, "ginghaosu" should be -- qinghoasu --.

Signed and Sealed this

Twenty-sixth Day of August, 2003

JAMES E. ROGAN
*Director of the United States Patent and Trademark Office*